(12) United States Patent
Zhu

(10) Patent No.: US 7,718,416 B1
(45) Date of Patent: May 18, 2010

(54) FUNGAL-DERIVED FORMULATIONS AND ASSOCIATED METHODS

(75) Inventor: Jai-Shi Zhu, San Diego, CA (US)

(73) Assignee: NSE Products, Inc., Provo, UT (US)

( * ) Notice: Subject to any disclaimer, the term of this patent is extended or adjusted under 35 U.S.C. 154(b) by 166 days.

(21) Appl. No.: 11/390,555

(22) Filed: Mar. 23, 2006

Related U.S. Application Data

(60) Provisional application No. 60/667,702, filed on Apr. 2, 2005.

(51) Int. Cl.
*C12N 1/14* (2006.01)
*C12N 1/00* (2006.01)
*A01N 63/04* (2006.01)

(52) U.S. Cl. .................. 435/254.1; 435/256.8; 435/911; 424/93.5

(58) Field of Classification Search ................ 435/256.8
See application file for complete search history.

(56) References Cited

U.S. PATENT DOCUMENTS 5,948,404 A * 9/1999 Taketomo et al. ........... 424/115

FOREIGN PATENT DOCUMENTS

| CN | 1513977 | * | 7/2004 |
| WO | WO 99/21961 | * | 5/1999 |

OTHER PUBLICATIONS

Smith, George. Smith's Introduction to Industrial Mycology. 7th edition. 1981. pp. 280-282.*

Holliday et al. "Analysis of quality and techniques for hybridization of medicinal fungus *Cordyceps sinensis* (Berk.) Sacc. (Ascomycetes)". International Journal of Medicinal Mushrooms, 2004. vol. 6, pp. 151-164.*

Jia-Shi Zhu, M.D., Ph..D. et al., "The Scientific Rediscovery of a Precious Ancient Chinese Herbal Medicine: *Cordyceps sinensis* Part I," The Journal of Alternative and Complementary Medicine, 1998, vol. 4, No. 3, pp. 289-303.

Jia-Shi Zhu, M.D., Ph..D. et al., "The Scientific Rediscovery of a Precious Ancient Chinese Herbal Regimen: *Cordyceps sinensis* Part II," The Journal of Alternative and Complementary Medicine, 1998, vol. 4, No. 4, pp. 429-457.

Jia-Shi Zhu et al., "Molecular Identification of *Cordyceps sinensis* Related Fungi," Abstract, article has not published, FASEB J., 2006, 20(4), A431.

Yinglan Guo et al, "Existence of multiple fungi in *Cordyceps sinensis*: Simultaneous isolation of *Hirsutella sinensis* and *Paecilomyces hepiali*," Abstract, article has not published, FASEB J., 2005, 19(5), A1033.

* cited by examiner

*Primary Examiner*—Vera Afremova
(74) *Attorney, Agent, or Firm*—Thorpe North & Western LLP

(57) ABSTRACT

Methods for stimulating in-vitro *paecilomyces hepiali* or *hirsutella sinensis* growth, and nutritional supplement formulations containing such fungal strains are disclosed and described. In some embodiments, such a method may include providing a an effective amount of a *p. hepiali* fungus strain for use as a stimulating agent on a culture medium for which *h. sinensis* is grown and regulating the temperature to induce and maintain the growth of the *h. sinensis* fungus. Alternatively, a *p. hepiali* fungus may be grown in a similar manner using *h. sinensis* as the stimulating agent. In some aspects, the growth of one fungus may be sequentially switched with the other in order to improve fungi potency.

21 Claims, 1 Drawing Sheet

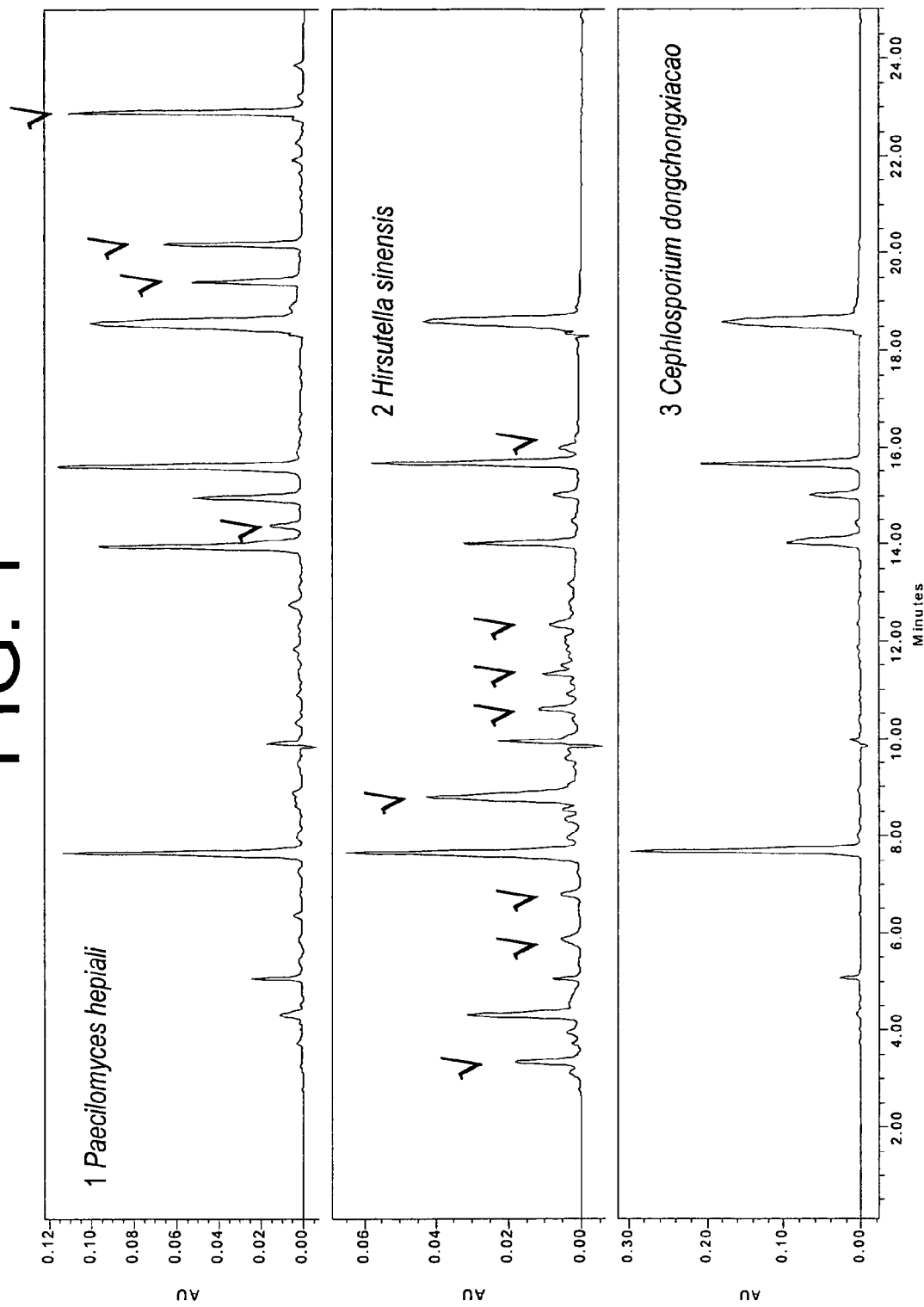

FUNGAL-DERIVED FORMULATIONS AND ASSOCIATED METHODS

This application claims the benefit of U.S. Provisional Patent Application Ser. No. 60/667,702, filed on Apr. 2, 2005, which is herein incorporated by reference in its entirety.

THE FIELD OF THE INVENTION

This invention relates to fungi found in the mycelia of *Cordyceps Sinensis*, and to methods and formulations associated therewith. Accordingly, the present invention involves the fields of botany, mycology, microbiology, nutritional and health sciences, and medicine.

BACKGROUND OF THE INVENTION

*Cordyceps sinensis* (*c. sinensis*) extracts have been used by Chinese people for many centuries as a part of traditional Chinese medicine, and is purported to have broad nutritional health benefits. *C. sinensis* is a parasitic fungus which grows by attaching to and feeding from one of several species of moth caterpillar living about six inches underground in the Tibetan plateaus. The fruiting body of *c. sinensis* is typically black and somewhat resembles the host body in appearance.

In 1993, *c. sinensis* was used as an integral part of the winning Chinese women's track team's diet regime. Since that time, the demand for *c. sinensis* has risen sharply. However, since the cultivation and harvest season for *c. sinensis* is only during late spring and fall of each year, demand continues to outweigh supply, and continuing research and development efforts have been hindered.

*C. sinensis* is reported to have a number of specific health imparting benefits, including anti-oxidant, anti-viral, anti-tumor, and anti-fatigue properties, as well as aiding in the treatment and prevention of hyperglycemia, renal dysfunction, liver disease, and in stimulation of immune, cardiovascular, respiratory, and reproductive responses. See, Zhu, Halpern, and Jones, "The Scientific Rediscovery of an Ancient Chinese Herbal Medicine: *Cordyceps sinensis*, Part I" The Journal of Alternative and Complementary Medicine, Vol. 4, pp. 289-303 (1998), and Zhu, Halpern, and Jones, "The Scientific Rediscovery of an Ancient Chinese Herbal Medicine: *Cordyceps sinensis*, Part II" The Journal of Alternative and Complementary Medicine, Vol. 4, pp. 429-457 (1998), incorporated herein by reference.

Many different fungi have been reportedly isolated from *c. sinensis*. However, there has been considerable dispute over the correctness of these reports, and the exact source of all reported fungi. Additionally, there has been much confusion as to the relationship and action between the various fungi found in the mycelium of *c. sinensis*.

In view of the truncated cultivation and harvest season for *c. sinensis*, a number of artificial culturing efforts have occurred. While such efforts have been moderately successful, it is now believed that cultured *c. sinensis* is less potent than the natural product.

In view of the foregoing, additional information concerning the characterization and relationship of the various fungi in *c. sinensis* mycelia, as well as methods for artificially reproducing such fungi which have the potency of naturally obtained fungal products continues to be sought.

SUMMARY OF THE INVENTION

Accordingly, the present invention provides nutritional supplement formulations including either a paecilomyces hepiali (*p. hepiali*) fungus or a hirsutella sinensis (*h. sinensis*), as well as methods for stimulating in-vitro growth thereof. In one embodiment, such a method may include providing an effective amount of a *h. sinensis* fungus to a culture medium to stimulate the *p. hepiali* growth. In an alternative embodiment, *h. sinensis* may be grown by providing an effective amount of a *p. hepiali* fungus to a culture medium to stimulate the growth of *h. sinensis*.

In another embodiment, a method for producing a *p. hepiali* fungus may include growing the *p. hepiali* on a culture medium by stimulating the growth with an effective amount of a *h. sinensis* fungus and harvesting the *p. hepiali* fungus. In an alternative embodiment, a method for producing a *h. sinensis* fungus may include growing the *h. sinensis* fungus on a culture medium by stimulating the growth with an effective amount of a *p. hepiali* fungus and harvesting the *h. sinensis* fungus.

In yet another embodiment, a method of identifying either *p. hepiali* or *h. sinensis* is provided. The method may be carried out by subjecting a material containing either fungus to a high-performance liquid chromatograph (HPLC) analysis. In the case of *p. hepiali* chromatographic peaks are observed at retention times of about 14 min, 19 min, 20 min, and 23 min. In the case of *h. sinensis* chromatographic peaks are observed at retention times of about 3 min, 6 min, 6.5 min, 9 min, 10.5 min, 11.5 min, 12.5 min, and 16 min.

In addition, the present invention also encompasses nutritional supplement formulations that may include a therapeutically effective amount of a *p. hepiali* fungus in combination with a therapeutically effective amount of a *h. sinensis* fungus. In one aspect, such fungi may be cultivated and obtained in accordance with the processes disclosed herein.

The present invention further encompasses methods of sequentially culturing fungi found in a *c. sinensis* mycelium as disclosed herein. In one embodiment such a method may include the steps of: 1) providing a culture medium suitable for growth of either paecilomyces hepiali or hirsutella sinensis; 2) adding a first growth stimulating agent of either paecilomyces hepiali or hirsutella sinensis to the culture medium; 3) growing a first target fungus of either paecilomyces hepiali, or hirsutella sinensis on the culture medium, whichever was not used as the first growth stimulating agent, at a suitable growth temperature therefor, until the first growth stimulating agent is exhausted; 4) introducing the first growth stimulating agent onto the growth medium for growth as a second target fungus on the culture medium using the first target fungus as a second growth stimulating agent; 5) growing the second target fungus on the growth medium under a temperature suitable for growth; and 6) harvesting the second target fungus. In some aspects, introduction of the first growth stimulating agent onto the growth medium is made by ceasing growth of the first target fungus prior to exhaustion of the first growth stimulating agent. In an additional aspect, the growth of the second target fungus may be halted prior to exhaustion of the second growth stimulating agent, and both the first and second target fungi are harvested from the growth medium. In yet another aspect, the growth of either the first or second target fungi may be ceased by changing the temperature to a temperature not suitable for growing the target fungi. In certain aspects, the temperature may be changed to a temperature suitable for growth of either the first or second stimulating agent as either the first or second target fungi. In further aspects, the first growth stimulating agent and second target fungus is paecilomyces hepiali, and the first target fungus and second growth stimulating agent is hirsutella sinensis. In an alternative aspect, wherein the first growth stimulating agent and second target is hirsutella sinensis, and the first target fungus and second growth stimulating agent is paecilomyces hepiali.

Thus, the more important features of the invention have been broadly outlined. The above-recited embodiments of the invention may be better understood from a consideration of the following detailed description. Also, other features of the present invention will become clearer from the detailed description that follows, taken with the claims, or may be learned by the practice of the invention.

BRIEF DESCRIPTION OF THE DRAWINGS

FIG. 1 illustrates a chromatograph analysis chart comparing chromatographic peaks of *Cordyceps sinensis, Paecilomyces hepiali* and *Hirsutella sinensis* fungi in accordance with one embodiment of the present invention.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

Definitions

In describing and claiming the present invention, the following terminology will be used.

The singular forms "a," "an," and "the" include plural referents unless the context clearly dictates otherwise. Thus, for example, reference to "a carrier" includes reference to one or more of such carriers, and reference to "an excipient" includes reference to one or more of such excipients.

As used herein, "formulation" and "composition" may be used interchangeably herein, and refer to a combination of two or more elements, or substances. In some embodiments a composition may include an active agent in combination with a carrier or other excipients, adjuvants, etc.

As used herein, "effective amount" refers to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, "pharmaceutically acceptable carrier," and "carrier" may be used interchangeably, and refers to any inert and pharmaceutically acceptable material with which a bioactive agent or a nutritional agent may be combined to achieve a specific dosage formulation for delivery to a subject. As a general principle, carriers must not react with the bioactive agent in a manner which substantially degrades or otherwise adversely affects the bioactive agent.

As used herein, "culture medium" refers to any nutrient providing medium which is suitable for the growth of one or more fungi. A variety of culture media for growing fungi which can be used with respect to the present invention are known to those skilled in the art. In general, a culture medium typically includes a nitrogen source, carbon source, phosphate materials, and inorganic salts. However, those of ordinary skill in the art will recognize various culture medium recipes most suitable for culturing various individual fungi.

As used herein, "*p. hepiali*" or "*hepiali*" refers to the fungus species *Paecilomyces hepiali* including all strains and hybrids thereof.

As used herein, "*h. sinensis*" or "*hirsutella*" refers to the fungus species of *Hirsutella sinensis* including all strains and hybrids thereof.

As used herein, "excipient" refers to substantially inert substance which may be combined with an active agent and a carrier to achieve a specific dosage formulation for delivery to a subject, or to provide a dosage form with specific performance properties. For example, excipients may include binders, lubricants, etc., but specifically exclude active agents and carriers.

As used herein, "subject" refers to a mammal that may benefit from the administration of a composition or method as recited herein. Most often, the subject will be a human.

As used herein, "administration," and "administering" refer to the manner in which an active agent, or composition containing such, is presented to a subject. Administration can be accomplished by various routes well-known in the art such as oral and non-oral methods.

As used herein, "oral administration" refers to a route of administration that can be achieved by swallowing, chewing, or sucking of an oral dosage form comprising the drug. Examples of well known oral dosage forms include tablets, capsules, caplets, powders, granulates, beverages, syrups, elixirs, confections, or other food items, etc.

As used herein, "target fungus" refers to a fungus, either *p. hepiali* or *h. sinensis* to be grown in or on a culture medium.

As used herein, "growth stimulating agent" refers to either a *p. hepiali* fungus or an *h. sinensis* fungus when used in a culture medium in order to stimulate the growth of the target fungus.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 400 should be interpreted to include not only the explicitly recited concentration limits of 0.5 and 400, but also to include individual concentrations within that range, such as 0.5, 0.7, 1.0, 5.2, 8.4, 11.6, 14.2, 100, 200, 300, and sub-ranges such as 0.5-2.5, 4.8-7.2, 6-14.9, 55, 85, 100-200, 117, 175, 200-300, 225, 250, and 300-400, etc. This interpretation should apply regardless of the breadth of the range or the characteristic being described.

The Invention

It has recently been discovered that two of the many fungi having positive health benefits contained in the mycelium of *c. sinensis* grow only within specific separate temperature ranges. Particularly, fermentation of *h. sinensis* and *p. hepiali* can occur at temperatures of from about 10° C. to about 15° C. and from about 20° C. to about 25° C., respectively. In addition the present inventors have now also discovered that the presence of one of these fungus strains stimulates the growth of the other, once the proper temperature conditions have been reached. In other words, the presence of each fungus in a single growth medium creates a symbiotic or interdependent growth stimulating relationship, where one fungus stimulates the growth of the other and vice versa once the proper temperature conditions have been reached.

Therefore, the temperature dependent nature for growth of *p. hepiali* and *h. hirsutella* may be used in concert with the newly discovered growth stimulating characteristics to induce a sequential fermentation process which can be employed for the in-vitro growth of either fungus. Accordingly, methods for stimulating in-vitro growth of a *p. hepiali* and *h. sinensis* are provided.

In one embodiment, such a method for stimulating growth of the *p. hepiali* fungus may include providing an effective amount of an *h. sinensis* fungus in a culture medium on which *p. hepiali* is to be grown. Alternatively, a *p. hepiali* fungus may be utilized in the in-vitro growth stimulation process of an *h. sinensis* fungus. The temperature sensitive nature of each fungi strain allows for the proper sequencing of growth. A low temperature range provides the proper fermentative conditions for the *h. sinensis* fungus. Exceeding these temperatures stunts the growth of *h. sinensis* and initiates the growth of the *p. hepiali* strain. This sequential process can be used in a cyclic manner allowing for the production of either fungus by altering the culture temperatures and with the additional presence of the other fungus strain. It has also been discovered that the above mentioned method provides maximized *p. hepiali* and *h. sinensis* fungi potencies.

Culturing fungi strains in-vitro can be accomplished with a wide range of growth media. Most effective fungal growth typically occurs on media that mimics the fungus' natural growth environment. However, in accordance with the present invention, any in-vitro growth medium that is suitable for culturing or fermentation of either *p. hepiali* or *h. sinensis* may be used. Often times a single growth medium will be suitable for culturing of both fungi. In some embodiments the growth stimulating agent fungus may be grown in a separate culture medium and later introduced to the medium containing a strain of the target fungus, or on which the target fungus is to be cultured, in order to stimulate its growth.

Typical ingredients for suitable culture mediums are known to those skilled in the art and often include a nitrogen source, carbon source, inorganic salt source and additional vitamin sources. Non-limiting examples of suitable nitrogen sources may include organic and inorganic nitrogen-containing substances such as peptone, corn steep liquor, meat extract, yeast extract, casein, urea, malt extract, amino acids, and ammonium and nitrate compounds. Examples of suitable carbon sources may include glucose (dextrose), xylose, sucrose, maltose, lactose, fructose, mannitol, sorbitol, glycerol, corn syrup and corn syrup. Examples of suitable inorganic salt sources may include phosphates, sulfates, magnesium, sodium, calcium, and potassium. These nutrients may be supplemented with, for example, one or more vitamins such as vitamin B and one or more minerals such as iron, manganese, cobalt, copper as desired. Other nutrient rich sources such as broths may be employed in accordance with certain embodiments of the present invention. For example, a soy broth may be an acceptable nutritious growth medium providing amino acids and other nitrogenous substances to the growth. In some embodiments of the present invention the growth medium may contain gelling and defoaming agents. For example, agar may be used as a gelling agent.

As will be recognized by those skilled in the art, variations in growth media compositions may be employed to produce the most conducive mycelia fungi growth environment. Accordingly, methods for stimulating *p. hepiali* or *h. sinensis* fungus growth may include, a slant culture medium having the ingredients of agar from about 0.5% to about 7%, peptone from about 0.1% to about 3%, mono-potassium phosphate 0.1% to about 3%, magnesium sulfate from about 0.01% to about 0.5%, bran from about 1% to about 10%, and the balance thereof may be water. Other mediums may be prepared such as a seed culture medium and a fermentation medium. A seed culture medium may contain glucose from about 0.5% to about 7%, peptone from about 0.1% to about 5%, mono-potassium phosphate from about 0.1% to about 1%, magnesium sulfate from about 0.01% to about 0.5%, bran from about 1% to about 10% and the balance thereof may be water. Further, a fermentation medium having the ingredients sucrose from about 0.5% to about 7%, glucose from about 0.5% to about 7%, peptone from about 0.1% to about 5%, mono-potassium phosphate from about 0.1% to about 1%, magnesium sulfate from about 0.01% to about 2%, soybean powder from about 0.5% to about 7%, soybean oil from about 0.01% to about 1%, and the balance thereof being water, may also be utilized by the present invention.

Culture and fermentative incubation times of each fungus may be dependant on both the growth medium and environmental conditions. According to one embodiment of the present invention, a growth medium may be inoculated with a *h. sinensis* strain and incubated for several hours to several days at temperatures in the desired ranges. For example, the fermentation time may be from 2 hours to 75 days. In another embodiment the fermentation time may be from 7 to 25 days. In contrast, other embodiments may include a growth medium which may be inoculated with a *p. hepiali* strain and incubated for several days. Accordingly, the embodiment may have a fermentation time from 1 to 10 days. In another embodiment the fermentation time may be from 3 days to 7 days.

Any environmental conditions including light, pH, humidity, and temperature which are conducive to the growth of the desired fungal strain may be used in connection with the present invention. As previously mentioned, the optimal temperature range for *p. hepiali* growth may be from about 20° C. to about 25° C. and the temperature range for *h. sinensis* growth may be from about 10° C. to about 15° C. The present invention encompasses methods for regulating the environmental conditions to promote desired fungi growth. These environmental conditions may be manipulated to mimic the natural environmental growth conditions of either fungi. In some embodiments, the environmental conditions may be regulated to induce the growth of *p. hepiali*. In other embodiments the environmental conditions may be controlled to stimulate growth of *h. sinensis*. Alternatively, the environmental conditions may be manipulated while using a single growth medium to stimulate the growth of *p. hepiali* and then manipulated to stimulate the growth *h. sinensis* sequentially, and may be manipulated in cyclic fashion to induce several periods of growth for each fungus.

In view of this point, a method for sequentially culturing fungi found in *c. sinensis* mycelium is provided. Such a method may include providing a culture medium suitable for growth of either *p. hepiali* or *h. sinensis* fungus. Subsequently, the medium may be inoculated with either fungus strain. Typically, both strains may be present on the growth medium one to be used as a growth stimulating agent, and the other as the target fungus for growth. The target fungus for growth (i.e. *p. hepiali*) may be grown at temperatures suitable for its growth until the growth stimulating agent (i.e. *h. sinensis*) is exhausted. Consequently, the target fungus strain may be used as a new growth stimulating agent to induce, facilitate, or accelerate the growth of the new target strain (which will most often be the previous growth stimulating agent). Additionally, the temperature should be adjusted to facilitate growth of the new target fungus. After growth, either the *p. hepiali* or *h. sinensis* fungus may be harvested depending on the method applied and the final target fungus.

Notably, in one aspect of the invention, the growth of the target fungus may be halted prior to exhaustion of the growth stimulating agent. In such a case, the temperature may be adjusted to now favor growth of the growth stimulating agent, and the growth stimulating agent now becomes the new target fungus for growth, and the previous target fungus becomes the new growth stimulating agent. Furthermore, when the time at which the fungi is harvested from the growth medium may be selected to yield a combination of fungi in any desired ratio, or to yield substantially on one fungus or the other. In this manner, both *p. hepiali* and *h. sinensis* fungal strains may be sequentially cultured, or fermented, until a strain, or combination of strains of desired potency and concentration can be obtained.

In addition to the methods of stimulating fungi growth recited herein, the present invention encompasses methods for producing a *p. hepiali* fungus which may include growing the *p. hepiali* fungus strain on a growth medium, which is stimulated by an effective amount of a *h. sinensis* strain and harvesting the *p. hepiali* fungus. Alternatively, an *h. sinensis* fungus may be produced by growing and stimulating the *h. sinensis* strain with an effective amount of *p. hepiali* and harvesting the *h. sinensis* fungus. Those of ordinary skill in the art will recognize that additional actions may be taken throughout the producing process in order to produce the desired fungus, such as, altering the growth media and controlling the environmental conditions to stimulate the desired growth. Furthermore, it should be noted that a pure or substantially pure *p. hepiali* or *h. sinensis* fungus may be produced through a sequential fermentation process. Alternatively, a product containing both strains may be achieved by halting the growth of the desired fungus prior to exhaustion of the other fungus.

Upon harvesting *p. hepiali* and *h. sinensis* fungi, whether each one is harvested separate or in the same growth medium, the resultant fungus may be incorporated into a nutritional supplement formulation. As noted in the background, *p. hepiali* and *h. sinensis* can produce many health imparting benefits. It has been recognized that a formulation which utilizes a therapeutically effective amount of either *p. hepiali* or *h. sinensis* or both in combination, having maximized potencies can promote these health imparting benefits to a subject.

While no limitation on the form of the nutritional supplement formulation has been made, in one embodiment the formulation may be the fungus in a solid oral dosage form. In another embodiment the oral dosage form may be a raw powder fungi extract. However, in other embodiments of the present invention the nutritional supplement formulation may be a variety of oral dosage forms that are well known to those of ordinary skill in the art, and specific formulation ingredients may be selected in order to provide a specific therapeutic result. For example and without limitation, oral dosage forms, such as beverages, powders, tablets, capsules, gel capsules, liquids, syrups, elixirs, and suspensions may be used. Accordingly, in one embodiment of the present invention, the composition may be a dosage form selected from the group consisting of beverages, effervescent beverages, liquids, syrups, elixirs, suspensions, tablets, powders, capsules, gel capsules, confections, candies, bars, lozenges, and combinations thereof. In a further embodiment of the present invention the beverage dosage form may utilize a powder form of the composition of the present invention, where the beverage formulation utilizes other ingredients, such as sweeteners, colorants and effervescent causing ingredients. In yet a further embodiment of the present invention, the composition may be administered by means of a transdermal matrix, liquid reservoir patches, or topical formulations, such as gels, creams, lotions, ointments and nasal sprays.

In addition to the fungi strains in the nutritional supplement formulation, other active ingredients may be included in the formulation of the present invention which impart a positive health benefit. As will be recognized by those skilled in the art, a wide variety of positive health benefit imparting ingredients may be selected from herbal and botanical extracts, as well as medicinal compounds and be added as desired in order to achieve a specific therapeutic result. Such additions may be made by the skilled artesian without undue experimentation.

Other ingredients such as a pharmaceutically acceptable carrier may be incorporated in the formulations of the present invention. In another embodiment suitable excipients may be added to the formulation. Examples of pharmaceutically acceptable carriers are polyethylene glycol, polyvinylpyrrolidone, a cellulose ether such as hydroxyalkyl cellulose (hydroxyethyl cellulose, hydroxypropyl cellulose, hydroxypropylmethyl cellulose, cellulose acetate trimellitate etc), and carboxyalkyl celluloses (carboxymethyl cellulose, carboxyethyl cellulose, etc) or a mixture thereof. Examples of suitable excipients are hydroxypropyl cellulose, carboxymethylcellulose, ethyl cellulose, methyl cellulose, their derivatives and salts. Additionally, other organic excipients which may be included in the formulation include but are not limited to polyethylene glycol, talc, lactose, starch, sorbitol, mannitol, polyvinylpyrrolidone and mixtures thereof.

The example provided below is illustrative of only one embodiment of identifying *p. hepiali* or *h. sinensis* strains according to the present invention. While the processing conditions and methods may be preferred, no limitation thereto is to be inferred.

EXAMPLE

Samples of *c. sinensis, p. hepiali*, and *h. sinensis* were analyzed and identified utilizing a high-performance liquid chromatograph (HPLC) system. The apparatus utilized was a HP 1100 having $C_8$ column, 5μ, and 15 cm long. A hot plate, 25 ml flask, 50 ml flask, HPLC grade water and HPLC acetonitrile were also used in the operation of the process.

A 300 mg sample of fungus was mixed with 20 ml of purified water in a 50 ml flask. The mixture was boiled and refluxed for 15 minutes on the hot plate. The sample was cooled to room temperature and filtered. Water was subsequently added to bring the supernatant of the sample to a total volume of 50 ml.

The chromatography conditions were set to a column temperature of 18° C. and a detection wavelength of 230 nm. A chart describing the gradient is provided (1) Gradient:

| | Time (min) | Flow (ml/min) | A % ($CH_3CN$) | B % (Water) |
|---|---|---|---|---|
| 1 | 0.0 | 1.0 | 5 | 95 |
| 2 | 5.0 | 1.0 | 40 | 60 |
| 3 | 18.0 | 1.0 | 60 | 40 |
| 4 | 22.0 | 1.0 | 90 | 10 |
| 5 | 24.5 | 1.0 | 90 | 10 |
| 6 | 25.0 | 1.0 | 5 | 95 |

Post elution times of 10 minutes in between samples was used.

The process was carried out under the chromatography conditions as describe above. A 20 µl sample was injected into HPLC column and analyzed and recorded by the chromatogram. Upon the completion the column was washed with 90% $CH_3CN$ for 20 minutes at a flow rate 1.0 ml/min.

FIG. 1, illustrates the results of the chromatographic analysis. FIG. 1 is a comparison chart of chromatographic peaks for a *c. sinensis*, *p. hepiali*, and *h. sinensis* samples. Notably, the *c. sinensis* has peaks at retention times of about 8 min, 14 min, 15 min, 15.5 min, and 18.5 min. *P. hepiali* and *h. sinensis* also have peaks at the same retention times; however, they also contain additional chromatographic peaks. Chromatographic peaks at retention times of about 14 min, 19 min, 20 min, and 23 min were observed for the *p. hepiali* sample. In addition, chromatographic peaks at retention times of about 3 min, 6 min, 6.5 min, 9 min, 10.5 min, 11.5 min, 12.5 min, and 16 min were observed for the *h. sinensis* sample. Accordingly, the chromatographic charts as shown in FIG. 1 may be compared to identify *p. hepiali* or *h. sinensis* strains.

It is to be understood that the above-described embodiments are only illustrative of the application of the principles of the present invention. Numerous modifications and alternative embodiments may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications may be made without departing from the principles and concepts set forth herein.

What is claimed is:

1. A method for stimulating in-vitro growth of a *Paecilomyces hepiali* fungus, comprising:
   providing an effective amount of a *Hirsutella sinensis* fungus in a culture medium on which *Paecilomyces hepiali* is grown.

2. The method of claim 1, wherein the *Paecilomyces hepiali* growth is halted prior to exhaustion of the *Hirsutella sinensis*.

3. A method for stimulating in-vitro growth of a *Hirsutella sinensis* fungus, comprising:
   providing an effective amount of a *Paecilomyces hepiali* fungus in a culture medium on which *Hirsutella sinensis* is grown.

4. The method of claim 3, wherein the *Hirsutella sinensis* growth is halted prior to exhaustion of the *Paecilomyces hepiali*.

5. The method of claim 1 or claim 3, further comprising regulating temperature, humidity, and light conditions of the in-vitro environment.

6. The method of claim 5, wherein the temperature is regulated to be in the range of about 10° C. to about 15° C.

7. The method of claim 5, wherein the temperature is regulated to be in the range of about 20° C. to about 25° C.

8. A method of producing a *Paecilomyces hepiali* fungus comprising the steps of:
   growing the *Paecilomyces hepiali* fungus on a growth medium and stimulating the growth with an effective amount of a *Hirsutella sinensis* fungus; and
   harvesting the *Paecilomyces hepiali* fungus.

9. The method of claim 8, wherein harvesting occurs prior to exhaustion of *Hirsutella sinensis* to yield a combination of *Paecilomyces hepiali* and *Hirsutella sinensis* fungi from a single growth medium.

10. A method of producing a *Hirsutella sinensis* fungus comprising the steps of:
    growing the *Hirsutella sinensis* fungus on a growth medium and stimulating the growth with an effective amount of a *Paecilomyces hepiali* fungus; and
    harvesting the *Hirsutella sinensis* fungus.

11. The method of claim 10, wherein harvesting occurs prior to exhaustion of *Paecilomyces hepiali* to yield a combination of *Paecilomyces hepiali* and *Hirsutella sinensis* fungi from a single growth medium.

12. A method of sequentially culturing fungi found in a *Cordyceps sinensis* mycelium comprising:
    providing a culture medium suitable for growth of *Paecilomyces hepiali*;
    adding a first growth stimulating agent of *Hirsutella sinensis* to the culture medium;
    growing a first target fungus of *Paecilomyces hepiali*, at a suitable growth temperature for *Paecilomyces hepiali*, until the Hirsutella sinensis is exhausted;
    introducing another amount of the *Hirsutella sinensis* onto the growth medium for growth as a second target fungus on the culture medium using the *Paecilomyces hepiali* as a second growth stimulating agent;
    growing the *Hirsutella sinensis* on the growth medium under a temperature suitable for growth for *Hirsutella sinensis*; and
    harvesting the *Hirsutella sinensis*.

13. The method of claim 12, wherein the step of introducing the *Hirsutella sinensis* onto the growth medium is made by ceasing growth of the *Paecilomyces hepiali* prior to exhaustion of the *Hirsutella sinensis*.

14. The method of claim 12, wherein the growth of the *Hirsutella sinensis* is halted prior to exhaustion of the *Paecilomyces hepiali*, and both the *Paecilomyces hepiali* and *Hirsutella sinensis* are harvested from the growth medium.

15. The method of any of claims 12-14, wherein growth of either the first or second target fungi is ceased by changing the temperature to a temperature not suitable for growing the target fungi.

16. The method of claim 15, wherein the temperature is changed to a temperature suitable for growth of either the first or second stimulating agent as either the first or second target fungi.

17. A method of sequentially culturing fungi found in a *Cordyceps sinensis* mycelium comprising:

provliding a culture medium suitable for growth of *Hirsutella sinensis*;

adding a first growth stimulating agent of *Paecilomyces hepiali* to the culture medium;

growing a first target fungus of *Hirsutella sinensis* on the culture medium, at a suitable growth temperature for *Hirsutella sinensis*, until the *Paecilomyces hepiali* is exhausted;

introducing another amount of the *Paecilomyces hepiali* onto the growth medium for growth as a second target fungus on the culture medium using the *Hirsutella sinensis* as a second growth stimulating agent;

growing the *Paecilomyces hepiali* on the growth medium under a temperature suitable for growth for the *Paecilomyces hepiali*; and harvesting the *Paecilomyces hepiali*.

18. The method of claim 17, wherein the step of introducing the *Paecilomyces hepiali* onto the growth medium is made by ceasing growth of the *Hirsutella sinensis* prior to exhaustion of the *Paecilomyces hepiali*.

19. The method of claim 17, wherein the growth of the *Paecilomyces hepiali* as the second target fungus is halted prior to exhaustion of the *Hirsutella sinensis*, and both the *Hirsutella sinensis* and *Paecilomyces hepiali* are harvested from the growth medium.

20. The method of any of claims 17-19, wherein growth of either the first or second target fungi is ceased by changing the temperature to a temperature not suitable for growing the target fungi.

21. The method of claim 15, wherein the temperature is changed to a temperature suitable for growth of either the first or second stimulating agent as either the first or second target fungi.

\* \* \* \* \*